United States Patent [19]
Leland et al.

[11] Patent Number: 5,846,485
[45] Date of Patent: Dec. 8, 1998

[54] ELECTROCHEMILUMINESCENT REACTION UTILIZING AMINE-DERIVED REDUCTANT

[75] Inventors: Jonathan Kent Leland, Laurel; Michael Joseph Powell, Gaithersburg, both of Md.

[73] Assignee: IGEN International Inc., Gaithersburg, Md.

[21] Appl. No.: 465,928

[22] Filed: Jun. 6, 1995

Related U.S. Application Data

[62] Division of Ser. No. 196,315, Apr. 15, 1994, which is a continuation of Ser. No. 266,914, Nov. 3, 1988, abandoned, which is a continuation-in-part of Ser. No. 858,354, filed as PCT/US87/00987 Apr. 30, 1986, Ser. No. 117,017, Nov. 4, 1987, and Ser. No. 369,560, Dec. 18, 1987, which is a continuation-in-part of Ser. No. 858,354, Apr. 30, 1986.

[51] Int. Cl.$^6$ .................................................. G01N 21/62
[52] U.S. Cl. ........................... 422/52; 436/800; 436/172; 436/84
[58] Field of Search ................. 435/5, 6, 7.1, 8, 435/808, 968, 975; 422/52, 90, 98; 436/501, 546, 800, 805, 806, 807, 84, 172; 935/78

[56] References Cited

U.S. PATENT DOCUMENTS

| | | |
|---|---|---|
| 3,319,132 | 5/1967 | Chandross . |
| 4,205,932 | 6/1980 | Cais . |
| 4,238,195 | 12/1980 | Bogulaski et al. . |
| 4,277,437 | 7/1981 | Maggio ................................... 422/61 |
| 4,280,815 | 7/1981 | Oberhardt et al. ..................... 435/8 X |
| 4,293,310 | 10/1981 | Weber ................................ 436/805 X |
| 4,378,344 | 3/1983 | Zahradnik et al. . |
| 4,412,064 | 10/1983 | Hinman .................................. 548/402 |
| 4,459,360 | 7/1984 | Marinkovich . |
| 4,514,508 | 4/1985 | Hirschfeld . |
| 4,539,507 | 9/1985 | Van Slyke . |
| 4,652,440 | 3/1987 | Paik ......................................... 424/1.1 |
| 4,659,839 | 4/1987 | Nicolotti et al. ........................ 548/546 |
| 4,687,732 | 8/1987 | Ward et al. . |
| 4,707,440 | 11/1987 | Stavrianopoulos .......................... 435/6 |
| 4,711,955 | 12/1987 | Ward et al. . |
| 4,745,076 | 5/1988 | Muller et al. ............................ 436/546 |
| 4,853,327 | 8/1989 | Dattagupta .................................. 435/6 |

FOREIGN PATENT DOCUMENTS

| | | |
|---|---|---|
| 0137457 | 4/1985 | European Pat. Off. . |
| WO 81/01883 | 7/1981 | WIPO . |
| 8602734 | 9/1986 | WIPO . |
| 8706706 | 5/1987 | WIPO . |
| 87/06706 | 11/1987 | WIPO ................................... 435/7.1 |

OTHER PUBLICATIONS

D. Ege et al, "Electrogenerated Chemiluminscent Determination of Ru (bpy)$_3^{2+}$ as low levels," *Anal. Chem.*, 56(13):2413–2417 (1984).

L. Faulkner et al, "Electrogenerated Chemiluminesce. VII. The Influence of an External Magnetic Field on Luminescence Intensity," *J. Amer. Chem. Soc.*, 94(3): 691–699 (1972).

(List continued on next page.)

*Primary Examiner*—Lyle Alfandary-Alexander
*Attorney, Agent, or Firm*—Curtis, Morris & Safford, P.C.; Barry Evans, Esq.; David Rubin, Esq.

[57] ABSTRACT

A composition suitable for use in an ECL assay wherein electromagnetic radiation emitted by said composition is detected, which composition comprises (a) a metal-containing ECL moiety which, when oxidized by exposure to an effective amount of electrochemical energy, is capable of being converted to an excited state from which electromagnetic radiation is emitted upon exposure of the excited ECL moiety to conditions sufficient to induce said emission; (b) an amine or amine moiety which, when oxidized by exposure to an effective amount of electrochemical energy, forms a strong reducing agent in said composition; and (c) an electrolyte capable of functioning as a medium in which said ECL moiety and said amine or amine moiety can be oxidized by exposure to electrochemical energy.

30 Claims, 4 Drawing Sheets

OTHER PUBLICATIONS

J. Noffsinger et al, "Generation of Chemiluminescence upon Reaction of Aliphatic Amines with This (2,2$^{1-}$bipyridine) ruthinium (III)," *Anal. Chem.,* 59(6):865–868 (1987).

Noffsinger et al., Anal. Chem. 1987, 59, 865.

Lytle et al., Photochem. Photobiol. 1971, 13, 123.

Faulkner et al., Electroanalytical Chemistry, A.J. Bard (Ed.), vol. 10, Marcel Dekker, N.Y., 1977, Ch. 1.

Tokel–Takvoryan et al., Chem. Phys. Litt., 1974, 25, 235.

Velasco et al.; Inorg. Chem., 1983, 22; 822.

Luong et al., J. Am. Chem. Soc. 1978, 100, 5790.

Abruna, J. Electrochem. Soc. 1985, 132, 842.

Abruna, J. Electroanal. Chem. 1984, 175, 321.

Freed et al., J. Am. Chem. Soc. 1971, 93, 2097.

Chang et al., J. Am. Chem. Soc. 1979, 99, 5399.

Ludvik et al., J. Electroanal. Chem. 1986, 215, 179.

Pragst et al., J. Electroanal. Chem. 1986, 197, 245.

Pragst et al., J. Electroanal. Chem. 1981, 119, 301.

Pragst et al., J. Electroanal. Chem. 1980, 112, 399.

Pragst et al., Electrogenerated Chemiluminescence in Mechanistic Investigations of Electroorganic Reactions, Part I. Cathodic Cleavage of Bis–(2,4,5–Triphenylimidazolyl)–1,2 "(Dibophyl)", No Date Supplied.

Rubenstein et al., "Electrogenerated Chemilumenescent Determination of Oxylate", Anal. Chem. 1983, 55, 9, 1580–82.

Tokel–Takvoryan et al., "Electrogenerated Chemiluminescence. XIII. Electrochemical and Electrogenerated Chemiluminescence Studies of Ruthenium Chelates", J. Am. Chem. Soc. 1973, 95, 20, 6582–89.

Hamblen et al., "Characteristics of an Electrically Controlled Fluorescent Dye Panel", IEEE Conference Record of 1972, Conference on display Devices, Oct. 11–12, (1972).

Wilson et al., "Electrogenerated Chemiluminescence of trans–Stilbene Derivatives", J. Electrochem. Soc.: Electrochemical Science and Technology (1981), vol. 128, No. 10, 2085–89.

Sato et al., "Quenching of Fluorescence in Europium–Diketone Chelate Solutions and its Application to Display Devices", Japanese Journal of Applied Physics, vol. 18, No. 7, 1979, 1295–1301.

Rozhitskii et al., "Steady–State Electrochemiluminescence in Solutions with Organometallic Electrolytes" J. Appl. Spectrosc. 1978, vol. 28, No. 2, 197–202.

Hemingway et al., "Electrogenerated Chemiluminescence. XXI. Energy Transfer from an Exciplex to a Rare Earth Chelate", J. Am. Chem. Soc. 1975, 97, 1, 200–01.

Itaya et al., "Electrogenerated Chemiluminescence with Solvated Electrons in Hexamethylphosphoramide. 2", J. Am. Chem. Soc. 1978, 100, 19, 5996–6002.

Tachikawa et al., "Electrogenerated Chemiluminescence XII. Magnetic Field Effects on ECL in the Tetracene–TMPD System; Evidence for Triplet–Triplet Annihilation of Tetracene", Chemical Physics Letters 1973, vol. 19, No. 2, 287–89.

Ziebig et al., "Intramolecular Exciplexes in the Electrogenerated Chemiluminescence of 1–Amino–3–Anthryl–(9)–Propanes", Journal of Luminescence 21 (1980), 353–66.

Wheeler et al, "A Silicon Phthalocyanine and a Silicon Naphthalocyanine: Synthesis, Electrochemistry, and Electrogenerated Chemiluminescence", J. Am. Chem. Soc. 1984, 106, 7404–10.

Tachikawa et al, "Electrogenerated Chemiluminescence. Effect of a Magnetic Field on the Delayed Fluorescence and ECL of Several Systems Involving Excimers of Exciplexes", Chemical Physics Letters 1974, vol. 26, No. 4, 568–73.

Keszthelyi et al., "Electrogenerated Chemiluminescence, XV. On the Formation of Excimers and Exciplexes in ECL", Chemical Physics Letters 1974, vol. 24, No. 2, 300–304.

Keszthelyi et al., "Electrogenerated Chemiluminescence, XVI. Effect of Supporting Electrolyte Concentration and Magnetic Field Effects in the 9, 10–Dimethylanthracene –tri–p–tolylamine in Tetrahydrofuran", Chemical Physics Letters 1973, vol. 23, No. 2, 219, 20–22.

Maloy et al, "Electrogenerated Chemiluminescence. II. The Rotating–Ring Disk Electrode and the Pyrene–N,N,N', N'–Tetramethyl–p–phenylenediamine System", J. Phys. Am. Chem. 1968, vol. 72, No. 12, 43, 48–50.

Springtschnik et al., Journal of the American Chemical Society, 99(15) 4947–54 (1977).

Ikariyama, Biochemical and Biophysical Research Communications, 128(2) at 987–92.

White, J. Amer. Chem. Soc. 104(25), 6891–6895 (1982).

Keszthelyi, Anal. Chem. 47(2), 249–255, (1975).

Caspar et al., (I): Inorganic Chemistry, 23, 2104–2109 (1984).

Caspar et al., (II): J. Phys. Chem., 87, 952–957, (1983).

Westmoreland, J. Amer. Chem. Soc. 105, 5952–5954, (1983).

Mitra et al., Chemical Abstracts 99:151025g (1983).

Kalyanasundaram, Chemical Abstracts 106:58729t (1987).

Salmon et al., J. Chem. Phys. 77(7), 337–3343, (1982).

Weber et al., "Photoelectroanalytical Chemistray: Possible Interference in Serum and Selective Detection of Tris (2,2–bypridine) ruthenium (II) in the Presence of Interferents," *Clinical Chemistry,* 29, 1665–1672 (1983).

Curtis et al., "Chemiluminescence: A New Method for Detecting Fluorescent Compounds Separated by Thin Layer Chromatography" *J. Chromatography* 134:343–350 (1977).

Minnich et al., "Enzyme Immunoassay for Detection of Salmonellae in Foods," *Appln. and Environ. Micro.* 43:1124–1127 (1982).

Thomason, B.M., "Current Status of Immunofluorescent Methodology for Salmonellae" *J. Food Prot.* 44:381–384 (1981).

Mattingly, J.A., "An Enzyme Immunoassay for the Detection of All Salmonella Using a Combination of a Myleloma Protein and Hybridoma Antibody," *J. Immunol. Meth.* 73:147–156 (1984).

Thompson, N.E., et al., "Detection of Staphylococcal enterotoxins by enzyme–linked immunosorbent assays and radio–immunoassays: Comparison of monoclonal and polyclonal antibody systems," *Appl. and Environ. Micro.,* submitted publication, May 1986.

Feng, P., and Hartman, P.A., "Fluorogenic assays for immediate confirmation of *Escherichia coli*.," *Appl. Environ. Microbiol.* 43:1320–1329 (1982).

Hussong, D., Colwell, R.R., and Weiner, R.M., "Rate of occurrence of false–positive results from total coliforms most–probable–number analysis of shellfish and estuaries," *Appln. Environ. Microbiol.* 40:981–983 (1980).

Hussong, D., Demare, J.M., Weiner, R.M., and Colwell, R.R., "Bacteria associated with false–positive most––probable–number coliform test results for shellfish and estuaries," *Appln. Environ. Microbio.* 41:35–45 (1981).

Lin, S., "Evaluation of coliform tests for chlorinated secondary effluents," *J. Water Pollut. Control Fed.* 45:498–506 (1973).

McKee, J.E., McLaughlin, R.T., and Lesgourgues, P., "Application of molecular filter techniques to the bacterial assay of sewage III. Effects of physical and chemical disinfection," *Sewage Ind. Waste* 30:245–252 (1958).

Mead, J.A.R., Smith, J.N., and Williams, R.T., "The biosynthesis of the glucuronides of umbelliferone and 4-methylumbelliferone and their use in fluorimetric determination of betafluorpnidase," *Biochem. J.* 61:569–574 (1955).

Olson, B.H., "Enhanced accuracy of coliform testing in seawater by modification of the most–probable–number method," *Appl. Environ. Microbiol.* 36:438–444 (1978).

Presnell, M.W., "Evaluation of membrane filter methods for enumerating coliforms and fecal coliforms in estuarine waters," *Proc. National Shellfish Santitation Workshop* 1974:127–131 (1974).

Presswood, W.G. and Strong, D.K., "Modification of the mFC medium by eliminating rosolic acid," *Appl. Environ. Microbiol.* 36:90–94 (1978).

Warr, G.W., and Marchalonis, J.J., "Purification of Antibodies," *Antibody as a Tool,* J. Wiley and Sons, New York, 59–96 (1982).

Maniatis, T., Fritsch, E.F., and Sambrook, J., *Molecular Cloning: A Laboratory Manual,* 150–160, Cold Spring Harbor Press, Cold Spring Harbor, New York (1982).

Kalyanasundarum et al., "Luminescence and Redox Reactions of the Metal–to–Ligand Charge–Transfer Excited State of Tricarbonyl Chloro–(Polypyridyl) Rhenium(I) Complexes," J. Chem. Soc., Faraday Trans 2 (1986) 82, 2401–2415.

L. Faulkner et al., "Electrogenerated Chemiluminescence. VII. The Influence of an External Magnetic Field on Luminescence Intensity" *J. Amer. Chem. Soc.* (94)3: 691–699 (1972).

J. Noffsinger et al., "Generating Chemiluminescence upon Reaction of Aliphatic Amines with Tris(2,2'–bipyridine)ruthenium (III)," *Anal. Chem.,* 59(6): 865–868 (1987).

Clark, H.F., Geldreich, E.E., Lester, H.L., and Kabler, P.W., The membrane filter in sanitary microbiology, *Public Health Rep.* 66:951–957 (1951).

ELECTROCHEMILUMINESCENT REACTION UTILIZING AMINE-DERIVED REDUCTANT

This application is a division of application Ser. No. 08/196,315 filed Apr. 15, 1994 which is a continuation of application Ser. No. 07/266,914 filed Nov. 3, 1988, which is a continuation-in-part of application Ser. No. 06/858,354 filed Apr. 30, 1986 and a continuation-in-part of PCT U.S. application Ser. No. 87/00987 filed Apr. 30, 1987, and a continuation-in-part of application Ser. No. 07/369,560, filed Dec. 18, 1987 and a continuation-in-part of application Ser. No. 07/117,017, filed Nov. 4, 1987. Application Ser. No. 07/369,560, filed Dec. 18, 1987 is the national phase of PCT U.S. application Ser. No. 87/00987, filed Apr. 30, 1987, which is a continuation-in-part of application Ser. No. 06/858,354, filed Apr. 30, 1986. Additionally, U.S. application Ser. No. 188,258 filed Apr. 29, 1988, U.S. application Ser. No. 789,113 filed Oct. 24, 1985, and U.S. application Ser. No. 266,882 entitled "Microparticulate-Based Nonseparation Binding Assay", naming Shah, Hall, Powell and Massey, filed on even date herewith (CMS Docket No. 370068-2390), are all incorporated by reference herein.

FIELD OF THE INVENTION

This application relates generally to electrochemiluminescent reactions, and more particularly to detecting the presence of an analyte of interest, and if desired quantitating the amount present, by measurement of electromagnetic radiation emitted by the system being investigated.

BACKGROUND OF THE INVENTION

In Noffsinger, J. B. et al., Anal. Chem. 1987, 59, 865, experiments relating to chemiluminescence obtained utilizing a reaction sequence involving amines and a ruthenium-containing luminophore ($Ru(bpy)_3^{3+}$) ("bpy" shall in all instances herein stand for "bipyridyl") were disclosed. See, also, Lytle, F. E. et al., Photochem. Photobiol. 1971, 13, 123. In this work, luminescence is achieved solely through chemical reactions, without triggering by electrochemical energy. While chemiluminescent techniques can be useful, electrochemiluminescent ("ECL") operations are preferable in several respects, for example: (1) there is greater control over the reaction sequence since the motive electrochemical energy can be interrupted with concomitant interruption of the reaction, whereas in chemiluminescent systems, the reaction sequence, once initiated, does not stop until completion; (2) luminophores can participate in multiple emissions whereas in chemiluminescent systems the luminophore only emits light once; (3) the apparatus employed is different from, and easier to work with than, that used in chemiluminescent techniques. However, successful generation of chemiluminescence with a particular system does not mean that the reaction system can be made to electrochemiluminesce, and thus the disclosure of Noffsinger et al. cannot fairly be extrapolated to predict similar results in an electrochemically stimulated system.

Early ECL reactions involved the annihilation of oppositely charged radical ions, produced by sequential oxidation and reduction at an electrode using a double potential step, for example, as described in Faulkner, L. R., et al., Electroanalytical Chemistry, A. J. Bard (Ed.), Vol. 10, Marcel Dekker, N. Y., 1977, Ch. 1; Tokel-Takvoryan, N. E., et al., Chem. Phys. Lett., 1974, 25, 235; Velasco, J. C., et al., Inorg. Chem. 1983, 22, 822; Luong, J. C., et al., J. Am. Chem. Soc. 1978, 100, 5790; Abruna, H. D., J. Electrochem. Soc. 1985, 132, 842; and Abruna, H. D., J. Electroanal. Chem. 1984, 175, 321. Upon homogeneous electron transfer between the sufficiently energetic and oppositely charged radicals, an excited state of one of the precursors can be formed, and subsequent emission by the species in the excited state occurs. Additionally, so-called energy deficient mechanisms involving triplet-triplet annihilations have been reported. See Freed, D. et al., J. Am. Chem. Soc. 1971, 93, 2097; Wallace, W. L. et al., J. Electrochem. Soc. 1978, 125, 1430.

In certain other ECL reactions, a luminophore has been used with an organic acid, such as an oxalate or pyruvate, to achieve electrogenerated chemiluminescence. Oxidative-reduction mechanisms, such as this, involve oxidation of $Ru(bpy)_3^{2+}$ (herein, "bpy" stands for "bipyridyl") and the organic acid. However, in certain situations systems of this nature are disadvantageous because the reaction leading to luminescence is conducted at a pH which is disadvantageously acidic. These systems are lacking in versatility, since their application to assaying of numerous biological interactions requires a departure from physiological solution conditions, such as pH, leading to a disruption of the immunochemistry of the assayed system. Illustratively, see Ege, D. et al., J. Anal. Chem. 1984, 56, 2413; Pubinstein, I. et al., J. Am. Chem. Soc. 1981, 103, 512; Chan, M. M. et al., J. Am. Chem. Soc. 1979, 99, 5399.

In certain articles by Pragst and co-workers, a fluorescent aromatic hydrocarbon, oxazole or oxadiazole has been subjected to electrochemical energy in the presence of imidazole or pyridine derivatives in order to achieve luminescence. See Ludvik, J. et al., J. Electroanal. Chem. 1986, 215, 179; Pragst, F. et al., J. Electroanal. Chem. 1986, 197, 245; Pragst, F. et al., J. Electroanal. Chem. 1981, 119, 301; and Pragst, F. et al., J. Electroanal. Chem. 1980, 112, 339. However, in each of these instances the luminophore was not a metal-containing substance, but rather was a non-metallic organic compound.

Provision of materials and methods for conducting ECL reactions utilizing metal-containing ECL moieties and amine reductants, to exploit the combined benefits of both while avoiding the disadvantages attendant upon the use of each in other systems, would be a significant technological advance.

OBJECTS OF THE INVENTION

It is an object of the present invention to provide materials and methods suitable for generating electrochemiluminescence.

It is another object of the present invention to provide materials and methods suitable for the conducting of ECL assays.

It is a further object of the present invention to provide methods and materials suitable for the detection of electrochemiluminescence, and thereby a wide variety of analytes of interest which may be present over a wide range of concentrations.

It is an additional object of the present invention to provide methods and materials which are suitable for conducting highly sensitive ECL assays for the detection and quantitation of very small concentrations of analytes of interest.

It is still another object of the present invention to provide materials and methods suitable for conducting precise, repeatable, highly sensitive ECL detection and/or quantitation of analytes present over a wide concentration range in aqueous environments, as well as organic environments.

It is yet another object of the present invention to provide materials and methods suitable for an ECL assay to detect and/or quantitate metal-containing ECL moiety.

It is still a further object of the present invention to provide methods and materials suitable for ECL detection and quantitation assays of an analyte of interest at a pH which does not disrupt the immunochemistry of an assayed system, and which are particularly suitable for detection and quantitation of an analyte of interest at a physiological pH.

These and other objects of the present invention will become even more readily apparent after consideration of the following description of the invention.

STATEMENT AND ADVANTAGES OF THE INVENTION

As will be seen from the discussion hereinafter, the present invention is a powerful tool which permits attainment of the objects set forth in the preceding section.

Thus, in one aspect the present invention is a composition suitable for use in an ECL assay, wherein electromagnetic radiation emitted by said composition is detected, which composition comprises (a) a metal-containing ECL moiety capable of being converted to an excited state from which electromagnetic radiation is emitted upon exposure of the excited ECL moiety to conditions sufficient to induce said emission;

(b) an amine or amine moiety which when oxidized forms a strong reducing agent; and (c) an electrolyte capable of functioning as a medium in which the ECL moiety and amine or amine moiety can be oxidized.

In another aspect, the invention relates to a reagent suitable for use in providing a composition for conducting an ECL assay wherein electromagnetic radiation is emitted by a composition comprising members selected from the group consisting of (i) a metal-containing ECL moiety capable of being converted to an excited state from which electromagnetic radiation is emitted upon exposure of the excited ECL moiety to conditions sufficient to induce said emission, (ii) an amine or an amine moiety which when oxidized forms a strong reducing agent, and (iii) an electrolyte capable of functioning as a medium in which said ECL moiety and said amine or amine moiety can be oxidized, said reagent comprising an amine or amine moiety and one of the other two members of said group.

In a further aspect, the present invention is directed to a kit for performing an ECL assay wherein electromagnetic radiation emitted by a composition is detected, which kit contains (i) a metal-containing ECL moiety capable of being converted to an excited state from which electromagnetic radiation is emitted upon exposure of the excited ECL moiety to conditions sufficient to induce said emission, (ii) an amine or an amine moiety which when oxidized forms a strong reducing agent, and (iii) an electrolyte capable of functioning as a medium in which said ECL moiety and said amine or amine moiety can be oxidized, said kit comprising at least one separate component in which one or more members of the group consisting of said ECL moiety (i), amine or amine moiety (ii), and electrolyte (iii) is included.

In still another aspect, the present invention relates to a method of generating emission of electromagnetic radiation, which comprises the steps of (a) forming a composition comprising (i) a metal-containing ECL moiety capable of being converted to an excited state from which electromagnetic radiation is emitted upon exposure of the excited ECL moiety to conditions sufficient to induce said emission; (ii) an amine or amine moiety which, when oxidized, forms a strong reducing agent; and (iii) an electrolyte capable of functioning as a medium in which said ECL moiety and said amine or amine moiety can be oxidized;

(b) exposing the composition under suitable conditions to an amount of electrochemical energy effective to induce the composition to emit electromagnetic radiation; and (c) detecting emitted electromagnetic radiation.

In an additional aspect, the invention also is directed to a method of detecting or quantitating an analyte of interest by ECL assay, which comprises (1) forming a composition comprising
  (a) a sample to be tested for the analyte of interest,
  (b) at least one substance selected from the group consisting of
    (i) additional analyte of interest or an analog of the analyte of interest,
    (ii) a binding partner of the analyte of interest or its said analog, and
    (iii) a reactive component capable of binding with (i) or (ii),
  (c) a metal-containing ECL moiety capable of being converted to an excited state from which electromagnetic radiation is emitted upon exposure of the excited ECL moiety to conditions sufficient to induce said emission, said ECL moiety being capable of entering into a binding interaction with the analyte of interest or a substance defined in (b)(i), (b)(ii), or (b)(iii);
  (d) an amine or an amine moiety which, when oxidized, forms a strong reducing agent, and
  (e) an electrolyte capable of functioning as a medium in which said ECL moiety and said species can be oxidized;

(2) exposing said composition to an amount of electrochemical energy effective to induce the composition to emit electromagnetic radiation; and (3) detecting emitted electromagnetic radiation.

In yet another aspect, the present invention relates to a system for ECL detection or quantitation of an analyte of interest in a sample, said system comprising:

(a) a sample,
(b) at least one substance selected from the group consisting of
  (i) added analyte of interest or an analog of the analyte of interest,
  (ii) a binding partner of the analyte of interest or its said analog, and
  (iii) a reactive component capable of binding with (i) or (ii), wherein one of said substances is linked, either directly or through one or more other molecules, to a metal-containing ECL moiety which is capable of being converted to an excited state from which electromagnetic radiation is emitted upon exposure of the ECL moiety to conditions sufficient to induce said emission (c) an amine or amine moiety which is capable of being converted to a strong reducing agent and an electrolyte;
(d) means for inducing the ECL moiety to emit electromagnetic radiation; and
(e) means for measuring the emitted radiation to determine the presence or quantity of the analyte of interest in the sample.

The "ECL moiety" or "metal-containing ECL moiety" is sometimes referred to as a "label", "label compound", "label substance", etc. It is within the scope of the invention for the species termed "ECL moiety", "metal-containing ECL moiety", "organometallic", "metal chelate", "transition metal chelate" and "rare earth metal chelate"—when utilized in certain of the composition, reagent, kit, method, or system embodiments in accordance with the invention—to be linked to other molecules such as an analyte or an analog thereof, a binding partner of the analyte or an analog thereof, a further binding partner of such aforementioned binding partner, or a reactive component capable of binding with the analyte, an analog thereof or a binding partner as mentioned above. The above-mentioned species can also be linked to a combination of one or more binding partners and/or one or more reactive components. Additionally, the aforementioned species can also be linked to an analyte or its analog bound to a binding partner, a reactive component, or a combination of one or more binding partners and/or one or more reactive components. It is also within the scope of the invention for a plurality of the aforementioned species to be bound directly, or through other molecules as discussed above, to an analyte or its analog.

It is similarly within the scope of the invention for the aforementioned "composition", hereinafter sometimes an "ECL composition", or a "system" to contain unstable, metastable and other intermediate species formed in the course of the ECL reaction, such as an ECL moiety in an excited state as aforesaid and the above-mentioned strong reducing agent.

Additionally, although the emission of visible light is an advantageous feature of certain embodiments of the invention it is within the scope of the invention for the composition (hereinafter sometimes "ECL composition") or system to emit other types of electromagnetic radiation, such as infrared or ultraviolet light, X-rays, microwaves, etc. Use of the terms "electrochemiluminescence", "electrochemiluminescent", "electrochemiluminesce", "luminescence", "luminescent" and "luminesce" in connection with the present invention does not require that the emission be light, but admits of the emission's being such other forms of electromagnetic radiation.

Substantial advantages are conferred on the practitioner of the present invention. The materials and methods in accordance with the invention provide an elegant technology for conducting the ECL detection and quantitation of an analyte of interest over a wide concentration range, down to a very small analyte concentration, in aqueous as well as organic environments. Good precision, and repeatability of detection and quantitation measurements are obtained. The utilization of metal-containing ECL moieties, especially metal chelates, in combination with amine-derived reductants, permits the practitioner of the invention to obtain advantages associated with use of each of these components, while avoiding disadvantages commonly encountered with other ECL techniques involving one or the other, but not both. Thus, the control over the reaction and the convenience of operation attendant upon using metal-containing species can be obtained without sacrifice of the capability of operation at a physiological pH. Conversely, the use of amine-derived reductants in the ECL interaction is advantageous: detection and quantitation functions can be performed without disrupting the immunochemistry of highly interesting biological systems which exist at physiological pH, but those functions do not involve use of organic luminophores that are incompatible with the aqueous environments of many of the highly interesting biological systems.

Furthermore, the present invention is useful in the detection and quantitation of numerous and highly varied analytes of interest as is discussed in the further description of the invention which follows.

Additionally, the versatility of the present invention is evident from the fact that it is not only useful in conducting heterogeneous assays, but also homogeneous assays. In this connection, heterogeneous assays are those in which ECL moiety linked directly or through one or more other molecules to the analyte of interest or its analog is separated, prior to exposure of such ECL moiety to electrochemical energy, from ECL moiety not linked to the analyte or its analog. Homogeneous assays, by way of contrast, are those in which there is no such separation before exposing the materials to electrochemical energy together. In the homogeneous assays of the present invention, electromagnetic radiation emitted when the ECL moiety is linked to the analyte or its analog differs from electromagnetic radiation emitted when the ECL moiety is not linked to the analyte or its analog. This can be achieved, for example, by sensing an increased or decreased emission amount corresponding to the presence of ECL moiety linked to analyte or its analog.

DESCRIPTION OF CERTAIN PREFERRED EMBODIMENTS

The invention, as well as additional objects, features and advantages thereof, will be understood more fully from the following detailed description of certain preferred embodiments.

The invention is useful in enabling the detection and quantitation of metal-containing compounds such as metal chelates, of amines and amine moieties, and of other analytes of interest which are capable of entering into a binding interaction. These reactions include, for example, antigen-antibody interactions, ligand-receptor interactions, DNA and RNA interactions, and other known reactions. In certain embodiments the invention relates to different materials and methods for qualitatively and quantitatively detecting the presence of analytes of interest in a multicomponent sample.

In addition to the metal-containing ECL moieties and the amines and amine moieties themselves, typical analytes of interest are a whole cell or surface antigen, subcellular particle, virus, prion, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, nonbiological polymer (preferably soluble), synthetic organic molecule, organometallic molecule, tranquilizer, barbituate, alkaloid, steroid, vitamin, amino acid, sugar, lectin, recombinant or derived protein, biotin, avidin, streptavidin, or inorganic molecule present in the sample. In one embodiment, the reagent is an ECL moiety conjugated to an antibody, antigen, nucleic acid, hapten, small nucleotide sequence, oligomer, ligand, enzyme, or biotin, avidin, streptavidin, Protein A, Protein G, or complexes thereof, or other secondary binding partner capable of binding to a primary binding partner through protein interactions.

Whole cells may be animal, plant, or bacterial, and may be viable or dead. Examples include plant pathogens such as fungi and nematodes. The term "subcellular particles" is meant to encompass, for example, subcellular organelles, membrane particles as from disrupted cells, fragments of cell walls, ribosomes, multienzyme complexes, and other particles which can be derived from living organisms. Nucleic acids include, for example, chromosomal DNA, plasmid DNA, viral DNA, and recombinant DNA derived from multiple sources. Nucleic acids also include RNA's, for example messenger RNA's, ribosomal RNA's and transfer RNA's. Polypeptides include, for example, enzymes, transport proteins, receptor proteins, and structural proteins such as viral coat proteins. Preferred polypeptides are enzymes and antibodies. Particularly preferred polypeptides are monoclonal antibodies. Hormones include, for example, insulin and T4 thyroid hormone. Pharmacological agents include, for example, cardiac glycosides. It is of course within the scope of this invention to include synthetic substances which chemically resemble biological materials, such as synthetic polypeptides, synthetic nucleic acids, and synthetic membranes, vesicles and liposomes. The foregoing is not intended to be a comprehensive list of the biological substances suitable for use in this invention, but is meant only to illustrate the wide scope of the invention.

Also, typically, the analyte of interest is present at a concentration of $10^{-3}$ molar or less, for example, at least as low as $10^{-18}$ molar.

The sample which may contain the analyte of interest, can be in solid, emulsion, suspension, liquid, or gas form, and can be derived from, for example, cells and cell-derived products, water, food, blood, serum, hair, sweat, urine, feces, tissue, saliva, oils, organic solvents or air. The sample can further comprise, for example, water, acetonitrile, dimethyl sulfoxide, dimethyl formamide, n-methyl-pyrrolidone or alcohols.

An essential feature of the invention is the utilization of metal-containing ECL moieties. Preferably, the ECL moiety is regenerative so that it can be repeatedly be induced to emit electromagnetic radiation, that is, it undergoes multiple emission events per molecule. This is a distinct advantage over conventional embodiments in which there is no "label" producing more than one emission event per molecule. (Note that it is within the scope of the invention to utilize additional "labels" such as radioactive isotopes, chemiluminescent molecules like luminol, etc.)

The ECL moieties utilized in accordance with the invention encompass organometallic compounds which emit electromagnetic radiation, such as visible light, as a result of electrochemical stimulation in accordance with the invention. Examples are 4,4',5',5 tetramethyl bipyridine Re(I)(4-ethyl pyridine)(CO)$_3$$^+$CF$_3$SO$_3$$^-$; and Pt(2-(2-thienyl) pyridine)$_2$.

Advantageously, the metal-containing ECL moiety is a metal chelate. The metal of that chelate is such that the chelate emits electromagnetic radiation, such as visible light, as a result of electrochemical stimulation in accordance with the invention. The metal of such metal chelates is, for instance, a transition metal (such as a transition metal from the d-block of the periodic table) or a rare earth metal. The metal is preferably ruthenium, osmium, rhenium, iridium, rhodium, platinum, indium, palladium, molybdenum, technitium, copper, chromium or tungsten, or lanthanum, neodymium, praesodymium or samarium. Especially preferred metals are ruthenium and osmium.

The ligands which are linked to the metal in such chelates are usually heterocyclic or organic in nature, and play a role in determining the emission wavelength of the metal chelate as well as whether or not the metal chelate is soluble in an aqueous environment or in an organic or other non-aqueous environment. The ligands can be polydentate, and can be substituted. Suitable polydentate ligands include aromatic and aliphatic ligands. Such aromatic polydentate ligands include aromatic heterocyclic ligands. Preferred aromatic heterocyclic ligands are nitrogen-containing, such as, for example, bipyridyl, bipyrazyl, terpyridyl, and phenanthrolyl. Suitable substituents include, for example, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, sulfur-containing groups, phosphorus containing groups, and the carboxylate ester of N-hydroxysuccinimide. The chelate can have one or more monodentate ligands, a wide variety of which are known to the art. Suitable monodentate ligands include, for example, carbon monoxide, cyanides, isocyanides, halides, and aliphatic, aromatic and heterocyclic phosphines, amines, stilbenes, and arsines.

Examples of suitable chelates are bis [(4,4'-carbomethoxy)-2,2'-bipyridine]-2-[3-(4-methyl-2,2'-bipyridine-4-yl)propyl]-1,3-dioxolane ruthenium (II); bis (2,2'bipyridine) [4-(butan-1-al)-4'-methyl-2,2'-bipyridine] ruthenium (II); bis (2,2'-bipyridine) [4-(4'-methyl-2,2'-bipyridine-4'-yl)-butyric acid] ruthenium (II); (2,2'-bipyridine) [bis-bis(1,2-diphenylphosphino)ethylene] 2-[3-(4-methyl-2,2'-bipyridine-4'-yl)propyl]-1,3-dioxolane osmium (II); bis (2,2'-bipyridine) [4-(4'-methyl-2,2'-bipyridine)-butylamine] ruthenium (II); bis (2,2'-bipyridine) [1-bromo-4-(4'-methyl-2,2'-bipyridine-4-yl)butane] ruthenium (II); and bis (2,2'-bipyridine) maleimidohexanoic acid, 4-methyl-2,2'-bipyridine-4'-butylamide ruthenium (II).

The function of the metal-containing ECL moiety in the present invention is to emit electromagnetic radiation as a result of introduction into the reaction system of electrochemical energy. In order to do this, the metal-containing ECL moiety must be capable of being stimulated to an excited energy state and also capable of emitting electromagnetic radiation, such as a photon of light, upon descending from that excited state. While not wishing to be bound by theoretical analysis of the mechanism of the metal-containing ECL moiety's participation, we believe that the ECL moiety is oxidized by the introduction of electrochemical energy into the reaction system and then, through interaction with the reductant present in the system, is converted to the excited state. This state is relatively unstable, and the metal-containing ECL moiety quickly descends to a more stable state. In so doing, the ECL moiety gives off electromagnetic radiation, such as a photon of light.

Typically, in assaying operations the metal-containing ECL moiety is linked directly or through one or more other molecules to the analyte of interest or an analog thereof. Analogs of the analyte of interest, which can be natural or synthetic, are typically compounds which have binding properties comparable to the analyte, but can also be compounds of higher or lower binding capability. When the metal-containing ECL moiety is linked to the analyte or said analog, through one or more other molecules, they are suitably a combination of one or more binding partners and/or one or more reactive components. Binding partners suitable for use in the present invention are well-known.

Examples are antibodies, enzymes, nucleic acids, cofactors and receptors. The reactive components capable of binding with the analyte or its analog, and/or with a binding partner, are suitably a second antibody or a protein such as Protein A or Protein G, or avidin or biotin or another component known in the art to enter into binding reactions.

The amount of metal chelate or other metal-containing ECL moiety incorporated in accordance with the invention will vary from system to system. Generally, the amount of such ECL moiety utilized is that amount which is effective to result in the emission of a detectable, and if desired quantitatable, amount of electromagnetic radiation, from the aforementioned composition. The detection and/or quantitation of an analyte of interest is typically made from a comparison of (i) the amount or wavelength of such electromagnetic radiation emitted by the ECL composition with (ii) data indicating the amount of electromagnetic radiation emitted when the concentration of the analyte of interest is known, such as in the form of a calibration curve. This, of course, assumes a homogeneous format. In the heterogeneous mode, a separation as discussed previously is carried out prior to ECL analysis.

As can be appreciated by one of ordinary skill in the art, the identity and amount of the metal-containing ECL moiety will vary from one system to another, depending upon prevailing conditions. The appropriate metal-containing ECL moiety, and sufficient amount thereof to obtain the desired result, can be determined empirically by those of ordinary skill in the art, once equipped with the teachings herein, without undue experimentation.

In a more specific embodiment a composition in accordance with the invention contains two or more different ECL moieties. Each of the ECL moieties can be induced to emit electromagnetic radiation of a wavelength different from the other moiety or moieties. In another embodiment of the invention, the ECL moieties can be species each of which is induced to emit electromagnetic radiation by exposure to energy of a value different from the energy value(s) at which the other moiety or moieties emit radiation. In this manner it is possible to determine two or more different analytes of interest that may be present in the sample under examination.

Another essential feature of the present invention is the utilization of an amine or amine moiety (of a larger molecule) which can be oxidized to convert it to a highly reducing species. Once again, while not wishing to be bound by a theoretical explanation of reaction mechanism, it is believed that the amine or amine moiety is also oxidized by electrochemical energy introduced into the reaction system. The amine or amine moiety loses one electron, and then deprotonates, or rearranges itself, into a strong reducing agent. This agent interacts with the oxidized metal-containing ECL moiety and causes it to assume the excited state discussed above. In order to carry out its role, the amine or amine moiety preferably has a carbon-centered radical with an electron which can be donated from such carbon, and an alpha carbon or conjugated carbon which can then act as a proton donor during deprotonation in order to form the reductant. The reductant provides the necessary stimulus for converting the oxidized metal-containing ECL moiety to its excited state, from which electromagnetic radiation is emitted.

Generally speaking, the reductant formed from the amine or amine moiety has a redox potential, $E_a$, which is defined in accordance with the following formula:

$$E_a \leq -hc/\lambda + K + E_m.$$

In the formula, h is Planck's constant, c is the speed of light, $\lambda$ is the wavelength characteristic of radiation emitted from the excited state of the metal-containing luminophore, K is the product of (i) the absolute temperature (in degrees Kelvin) of the environment in which the ECL interaction takes place and (ii) the change in entropy as a result of the ECL reaction, and $E_m$ is the redox potential of the ECL moiety. Normally, the product of temperature and change in entropy is approximately 0.1 eV.

The following calculation explicates the use of the formula $$E_a \leq -hc/\lambda + K + E_m \tag{1}$$

for determining the minimum reducing power of the oxidized, deprotonated amine or amine moiety, and thus in the selection of suitable amines or amine moieties.

For $Ru(bpy)_3^{2+}$ as ECL moiety, the wavelength of emission, $\lambda$, is 620 nM. See Tokel N. E., et al., J. Am. Chem. Soc. 94, 2862 (1972). $E_m$ is 1.3 V as compared to NHE (NHE is a normal hydrogen reference electrode) and $$\frac{hc}{\lambda} = \frac{(4.13 \times 10^{-15} eV - \sec)(3 \times 10^{10} cm/sec)}{6.2 \times 10^{-5} cm} \tag{2}$$

$$= 2.0 \, eV \text{ (electron volts)}.$$

See Wilkins, D. H., et al., Anal. Chem. Acta. 9, 538 (1953). K is taken to be 0.1 eV. See Faulkner, L. R., et al., J. Am. Chem. Soc. 94, 691 (1972). Substituting these values into equation 1 gives $$E_a \leq -2.0 + 0.1 + 1.3 \tag{3}$$

$$E_a \leq -0.6 \tag{4}$$

Equation 4 implies that the reducing strength of the amine-derived reductant must be equal to or more negative than −0.6 V as compared to NHE. (Note that when referring to potential differences, i.e. $E_a$ or $E_m$, the unit of potential is Volts, and the terms $hc/\lambda$ and K have an energy unit which is eV; however, the conversion from potential difference to eV is unity.)

A wide range of amines and amine moieties can be utilized in practicing the present invention. Generally, the amine or amine moiety is chosen to suit the pH of the system which is to be ECL analyzed. Another relevant factor is that the amine or amine moiety should be compatible with the environment in which it must function during analysis, i.e., compatible with an aqueous or non-aqueous environment, as the case may be. Yet another consideration is that the amine or amine moiety selected should form a reductant under prevailing conditions which is strong enough to reduce the oxidized metal-containing ECL moiety in the system.

Amines which are advantageously utilized in the present invention are aliphatic amines, such as primary, secondary and tertiary alkyl amines, the alkyl groups of each having from one to three carbon atoms, as well as substituted aliphatic amines. Tripropyl amine is an especially preferred amine as it leads to, comparatively speaking, a particularly high-intensity emission of electromagnetic radiation, which enhances the sensitivity and accuracy of detection and quantitation with embodiments in which it is used. Also suitable are diamines, such as hydrazine, and polyamines, such as poly(ethyleneimine). The amine substance in the present invention can also be an aromatic amine, such as aniline. Additionally, heterocyclic amines such as pyridine, pyrrole, 3-pyrroline, pyrrolidine and 1,4-dihydropyridine are suitable for certain embodiments.

The foregoing amines can be substituted, for example, by one or more of the following substituents: —OH, alkyl, chloro, fluoro, bromo and iodo, —SO₃, aryl, —SH, —COOH, ester groups, ether groups, alkenyl, alkynyl, —N₂⁺, cyano, epoxide groups and heterocyclic groups. Also, protonated salts, for instance, of the formula R₃N—H⁺, wherein R is H or a substituent listed above are suitable.

Amine moities corresponding to the above-mentioned amines (substituted or unsubstituted) are also preferred.

As previously mentioned, tripropyl amine (or an amine moiety derived therefrom) is especially preferred because it yields a very high light intensity. This amine, and the other amines and amine moieties useful in the present invention, work suitably well at pH of from 6 to 9. However, tripropyl amine gives best results at a pH of from 7–7.5. Examples of additional amines suitable for practicing the invention are triethanol amine, triethyl amine, 1,4-diazabicyclo-(2.2.2)-octane, 1-piperidine ethanol, 1,4-piperazine-bis-(ethane-sulfonic acid), and tri-ispropyl amine.

Typically, the metal-containing ECL moiety utilized in the present invention is the reaction-limiting constituent. Accordingly, it is also typical that the amine or amine moiety is provided in a stoichiometric excess in respect of the ECL moiety. Illustratively, the amine or amine moiety is employed in a concentration of 50–150 mM. For utilization at a pH of approximately 7, a concentration of 100 mM is often advantageous. In certain embodiments, the upper limit on amine or amine moiety concentration is determined by the maximum solubility of the amine or amine moiety (or balance of the molecule of which it is a part) in the environment in which it is being used, for example in water. In general, the amount of amine or amine moiety employed is that which is sufficient to effect the transformation of the oxidized metal-containing ECL moiety into its excited state so that electromagnetic radiation emission occurs.

Those of ordinary skill in the art, equipped with the teachings herein, can determine empirically the identity and/or amount of amine or amine moiety advantageously used for the particular system being analyzed, without undue experimentation.

As noted above, the ECL moiety incorporated in accordance with the present invention is induced to emit electromagnetic radiation by stimulating it into an excited state. This is accomplished by exposing the composition in which the ECL moiety is incorporated to electrochemical energy. The potential(s) at which oxidation of the ECL moiety and the amine or amine moiety occur(s) depend(s) upon the chemical structures thereof, as well as factors such as the pH of the system and the nature of the electrode used to introduce electrochemical energy. It is well known to those of ordinary skill in the art how to determine the optimal potential and solution conditions for an ECL system.

Of course, in order to operate a system in which an electrode introduces electrochemical energy, it is necessary to provide an electrolyte in which the electrode is immersed and the ECL moiety and amine or amine moiety are contained. The electrolyte is a phase through which charge is carried by ions.

Generally, the electrolyte is in the liquid phase, and is a solution of one or more salts or other species in water, an organic liquid or mixture of organic liquids, or a mixture of water and one or more organic liquids. However, other forms of electrolyte are also useful in certain embodiments of the invention. For example, the electrolyte may be a dispersion of one or more substances in a fluid e.g., a liquid, a vapor, or a supercritical fluid—or may be a solution of one or more substances in a solid, a vapor or supercritical fluid.

The above-mentioned supercritical fluid is a dense gas maintained above its critical temperature, i.e., the temperature above which it cannot be liquified by any pressure. Supercritical fluids are less viscous and diffuse more readily than liquids. Examples of supercritical fluids which can be useful in practicing the present invention are carbon dioxide, and certain alkanes such as methane, ethane and propane. The conditions at which supercritical behavior is exhibited are known in the art. See, for instance, Smith U.S. Pat. No. 4,582,731 granted Apr. 15, 1986. Utilization of supercritical fluids can be advantageous; for instance, in certain embodiments of the invention the solubility of various analytes of interest can be increased in a supercritical fluid. Also, the solubility of the ECL moiety and the amine or amine moiety can, in some embodiments, be more easily controlled in a supercritical fluid. Furthermore, sensitivity can in some cases be improved because of the higher diffusion coefficient of various species in these fluids.

In the case of compositions in accordance with the present invention which are aqueous, the electrolyte is aqueous, e.g., a solution of a salt in water. The salt can be a sodium salt or a potassium salt preferably, but incorporation of other cations is also suitable in certain embodiments, as long as the cation does not interfere with the ECL interaction sequence. The salt's anion may be a phosphate, for example, but the use of other anions is also permissible in certain embodiments of the invention—once again, as long as the selected anion does not interfere with the ECL interaction sequence.

The composition can also be non-aqueous. While supercritical fluids can in certain instances be employed advantageously, it is far more typical to utilize an electrolyte comprising an organic liquid in a non-aqueous composition. Like an aqueous electrolyte, the non-aqueous electrolyte is also a phase through which charge is carried by ions. Normally, this means that a salt is dissolved in the organic liquid medium. Examples of suitable organic liquids are acetonitrile, dimethylsulfoxide (DMSO), dimethylformanide (DMF), methanol, ethanol, and mixtures of two or more of the foregoing. Illustratively, tetraalkylammonium salts, such as tetrabutylammonium tetrafluoroborate, are soluble in organic liquids and can be used with them to form non-aqueous electrolytes.

The electrolyte is, in certain embodiments of the invention, a buffered system. Phosphate buffers are often advantageous. Examples are an aqueous solution of sodium phosphate/sodium chloride, and an aqueous solution of sodium phosphate/sodium fluoride.

The formulation of electrolytes, including buffered systems, and a determination of suitable amounts of electrolyte for use in practicing the invention is within the skill of the art, once the practitioner is equipped with the teachings herein.

Utilization of the aforementioned materials in the present invention permits its practitioner to induce the emission of electromagnetic radiation from an ECL composition in accordance with the method embodiments of the invention.

In one broad aspect, the inventive method is in the generation of electromagnetic radiation from an ECL composition as described herein.

This is accomplished by combining one or more metal-containing ECL moieties, one or more amines and/or amine moieties and a compatible electrolyte to form a composition into which electrochemical energy can be introduced with the result that electromagnetic radiation is emitted. The composition is subjected to an amount of electrochemical energy which is effective to induce the composition to emit electromagnetic radiation.

By inducing the composition to emit electromagnetic radiation we mean generating an excited state of the ECL moiety in the composition, which excited ECL moiety gives off electromagnetic radiation—for instance, luminesces at wavelengths from about 200 nanometers to about 900 nanometers at ambient temperatures. This excited state is achieved by oxidizing the ECL moiety. As previously noted, the potential at which the oxidation of the ECL moiety occurs depends upon its chemical structure as well as factors such as the pH of the composition and the nature of the electrode used. Once the ECL moiety is excited, it emits electromagnetic radiation upon interaction with the strong reductant discussed previously. Determination of the optimal potential and emission wavelength for an ECL composition is within the ordinary skill of the art once it is in possession of the teachings herein. The amount of electromagnetic radiation emitted by the ECL moiety as it descends from the excited state can be measured directly as an indication of the amount of analyte present. Alternatively, the electromagnetic radiation emitted when the ECL moiety descends from the excited state can be utilized to trigger a detectable event (or one step in a sequence of steps culminating in a detectable event) which is measured, rather than the radiation emitted by the ECL moiety itself.

Radiation emitted by the ECL composition is detected using suitable means in order to permit a qualitative or quantitative determination of the analyte of interest.

This determination can be made visually in certain embodiments, but advantageously either as a continuous rate-based measurement, or as an accumulation of the ECL signal over a long period of time. For example, rate-based measurement methods can be performed with photomultiplier tubes, photodiodes or phototransistors to produce electric currents proportional in magnitude to the incident light intensity, or by using charge couple devices, whereas examples of cumulative methods are the integration of rate-based data and the use of photographic film to provide cumulative data directly.

The composition is formulated in order to obtain the desired pH, concentration of ECL moiety, concentration of amine or amine moiety, and electrolyte. In this connection, the metal-containing ECL moieties, amines and amine moieties, electrolytes, and suitable and preferred amounts and concentrations thereof in the composition, are as described elsewhere herein.

The composition can be made by combining its individual ingredients. However, it is often more advantageous to utilize one or more reagents containing a combination of various substances from which the composition is made. This measure facilitates the maintenance of uniformity in the compositions formulated according to the invention, which contributes to the reliability and repeatability achieved with practice of the invention.

Accordingly, a reagent suitable for formulation of the composition can comprise the metal-containing ECL moiety and an amine or amine moiety which is to be incorporated in the composition. Alternatively, the reagent can comprise the metal-containing ECL moiety and the electrolyte selected, or the amine or amine moiety and the electrolyte selected. Whichever reagent is chosen can be combined with the balance of the ingredients necessary to formulate the composition. One or more of those ingredients can also be contained in another reagent. For instance, a reagent comprising a metal-containing ECL moiety/electrolyte combination can be mixed with another reagent comprising an amine or amine moiety/electrolyte combination to yield the desired composition.

In a preferred embodiment, reagent comprising the amine or amine moiety and the electrolyte is combined with another reagent comprising the ECL moiety.

The formation of the composition is suitably accomplished with a kit comprising one or more reagent components necessary for the formulation step. Thus, the overall kit contains (i) a metal-containing ECL moiety as described previously, (ii) an amine or amine moiety as described previously, and (iii) and electrolyte as described previously. An attractive aspect of packaging ingredients used to formulate the composition in a kit is that standardized ingredients, provided as one or more reagents for convenience, can be employed to improve the reliability and repeatability of practice of the invention. Use of reagents and other materials in kit form is additionally advantageous in that it offers a way to minimize the possibility of degradation of the ingredients before use. This is a result of the kit format's being capable of structuring so as to avoid combinations in which such degradation might occur.

Accordingly, the composition can be formulated from a kit in which any two members of the group consisting of the metal-containing ECL moiety, the amine or amine moiety, and the electrolyte can be included in a first separate component and the remaining member of the group in a second separate component. (The component(s) of the kit is or are typically kept separate by enclosing each in its own vial so as to eliminate cross-contamination prior to combination.) An alternative is a kit comprising a first separate component including any two members of the aforementioned group, and a second separate component including the remaining member of the group and either one of the other members of the group. Another alternative is a kit which comprises three separate components, each of which includes a different one of the three members of the aforementioned group. In yet another format, the kit can comprise a first separate component including all three members of the group, and a second separate component including any one or two of the members of that group; such a kit can also further comprise a third separate component including one or two members of the group.

More specifically, in an advantageous embodiment, the first separate component of a kit includes the metal-containing ECL moiety and the amine or amine moiety, and the second separate component includes the electrolyte. Alternatively, a first separate component of the kit contains the ECL moiety and the electrolyte and the second separate component contains the amine or amine moiety. In a particularly preferred embodiment, the first separate kit component includes the amine or amine moiety and the electrolyte, and the second separate component includes the metal-containing ECL moiety.

As mentioned above, with the present invention the emission of electronmagnetic energy is brought about by exposing a composition as discussed above to an amount of electrochemical energy effective to induce such emission. Advantageously, the emission is induced by exposing the composition and thus the metal-containing ECL moiety therein to a voltammetric working electrode. The ECL reactive mixture is, accordingly, controllably triggered to emit light or other electromagnetic radiation by a voltage impressed on the working electrode at a particular time and in a particular manner effective to result in such generation of light or other form of electromagnetic radiation as is desired. The necessary voltage can be derived empirically by one of ordinary skill in the art, equipped with the teachings herein, without undue experimentation.

Figure 1:
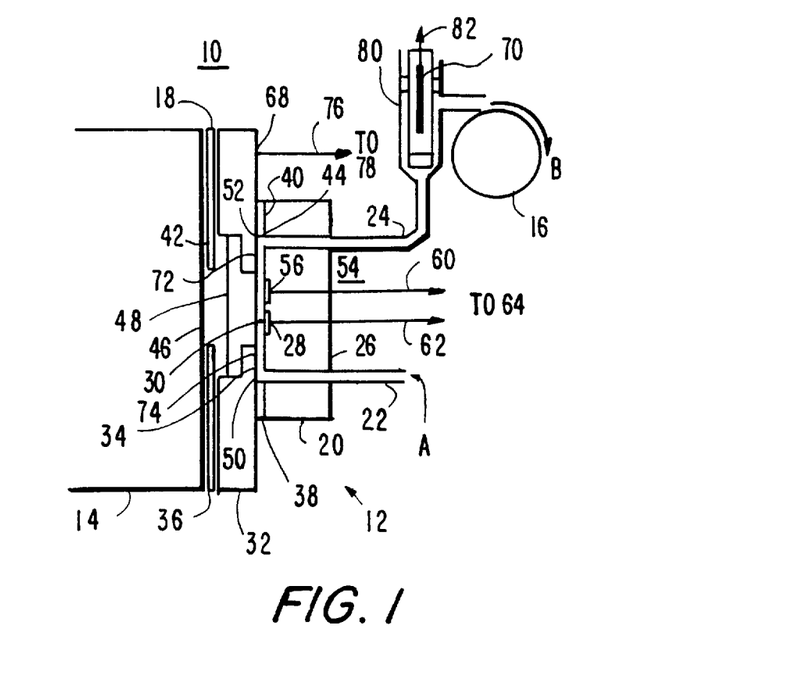
FIG. 1 is a schematic drawing of a cell suitable for inducing the emission of electrochemiluminescence in accordance with the present invention.
Figure 2:
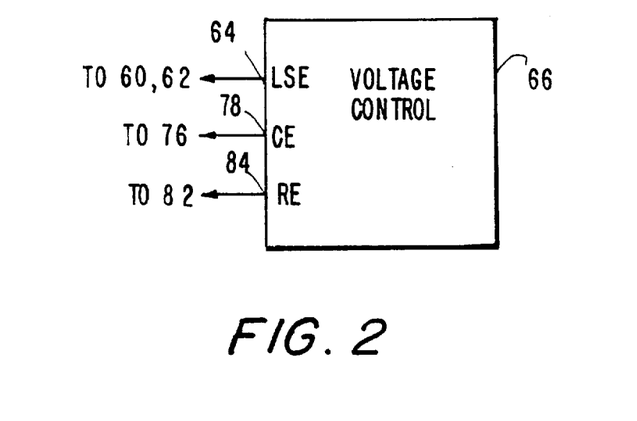
FIG. 2 is a simplified diagram of a voltage control apparatus for use with the cell illustrated in FIG. 1.

The method of the invention is further explicated in connection with the discussion of apparatus suitable for carrying it out, as illustrated in FIGS. 1 and 2.

FIG. 1 discloses an advantageous apparatus for generating electrochemiluminescence. However, the methods of the present invention are not limited to application with apparatus 10, but rather can be implemented with other types of apparatus including a working electrode or other triggering surface to provide electrochemical energy to trigger electrochemiluminescence. While the methods of the invention can be carried out in a static or flow-through mode, apparatus 10 is a flow-through cell, which provides distinct advantages for many types of ECL operation, for example, handling of many types of samples including binding assay samples.

Apparatus 10 includes an electrochemical cell 12, a light detection/measurement device 14, which can advantageously be a photomultiplier tube (PMT), photodiode, charge coupled device, photographic film or emulsion or the like, and a pump 16, which is advantageously a peristaltic pump, to provide for fluid transport to, through and from cell 12. Alternatively, a positive displacement pump may be used. A shutter mechanism 18 is provided between cell 12 and PMT 14 and is controllably operated to open only so far as to expose PMT 14 to cell 12 during periods of measurement of electrochemiluminescence. Shutter mechanism 18 can be closed, for example, during maintenance. Advantageously, included in apparatus 10 but not shown in FIG. 1 (for purposes of simplicity and clarity) is a lightproof housing inside of which the various components of the apparatus can be disposed to shield PMT 14 from any external light during measurements of electrochemiluminescence.

Cell 12 itself includes a first mounting block 20 through which passes an inlet tube 22 and an outlet tube 24, advantageously constructed of stainless steel. Mounting block 20 has a first, outer surface 26 and a second inner surface 28 defining one side of a sample-holding volume 30 in which cell 12 holds the cleaning and/or conditioning and/or measurement solutions during corresponding operations of apparatus 10. Inlet and outlet tubes 22, 24 pass through mounting block 20 from outer surface 26 to inner surface 28 and open into sample-holding volume 30. A second mounting block 32, advantageously constructed of stainless steel also has a first, outer surface 34 and a second, inner surface 36. Second mounting block 32 is separated from first mounting block 20 by an annular spacer 38, advantageously constructed of Teflon or other non-contaminable material. Thus, outer surface 34 of mounting block 20 defines part of the second side of the sample-holding volume 30. Spacer 38 has an outer portion 40 and a central aperture 42, the inner edge 44 of which defines the sidewall of sample-holding volume 30. Outer portion 40 seals the inner surface 28 of first mounting block 20 to outer surface 34 of second mounting block 32 to prevent any solution from passing out from sample-holding volume 30 between the two surfaces 28, 34. Mounting block 32 further has a central aperture 46 in which a window 48 is seal-fitted to define the rest of the second side of sample-holding volume 30 as a continuation of outer surface 34. Window 48 is formed of a material which is substantially transparent at the wave length of ECT, light generated by the system in sample-holding volume 30. Window 48 is therefore advantageously formed of glass, plastic, quartz or the like.

Inlet tube 22 intersects sample-holding volume 30 at a first end 50 thereof adjacent to spacer 38, and outlet tube 24 intersects sample-holding volume 30 at a second end 52 thereof adjacent to spacer 38. Combination of inlet tube 22, sample-holding volume 30 and outlet tube 24 thereby provides a continuous flow path for the narrow, substantially laminar flow of a solution to, through and from cell 12.

Mounted on inner surface 28 of first mounting block 20 is a working electrode system 54 which, in the illustrated embodiment, includes first and second working electrodes 56 and 58. In other embodiments, a single working electrode may advantageously be provided or only electrode 56 may be a working electrode. Working electrodes 56, 58 are where the electrochemical and ECL reactions of interest can take place. Working electrodes 56, 58 are solid voltammetric electrodes and therefore can advantageously be constructed of platinum, gold, carbon or other materials which are effective for this purpose. Wire connectors 60, 62 connected to working electrodes 56, 58 respectively, pass out through first mounting block 20.

Connectors, 60, 62 are both connected to a first, "working electrode" terminal 64 of a voltage control 66, illustrated in FIG. 2. Voltage control 66 advantageously operates in the matter of a potentiostat to supply voltage signals to working electrodes 56, 58 and optionally to measure current flowing therefrom during measurement of electrochemiluminescence. Alternatively, connectors 60, 62 may be connected to separate terminals of voltage control 66 for individual operation.

The potentiostat operation of voltage control 66 is further effected through a counter electrode 68 and, optionally advantageously, a reference electrode 70. In the illustrated embodiment, mounting block 32 is made of stainless steel and counter electrode 68 consists in exposed surfaces 72, 74 of mounting block 32. Counter electrode 72, 74 and working electrodes 56, 58 provide the interface to impress the potential on the solution within sample-holding volume 30 which energizes the reactions of interest and triggers electrochemiluminescence in the sample and/or provides energy for cleaning and conditioning the surface of cell 12. Counter electrode 72, 74 is connected by a wire connector 76, to a second "counter electrode" terminal 78 of voltage control 66.

Reference electrode 70 provides a reference voltage to which the voltage applied by the working electrodes 56, 58 is referred, for example, +1.2 volts versus reference. Reference electrode 70 is advantageously located in outlet tube 24 at a position 80 spaced from cell 12 and is connected through a wire connector 82 to a third "reference electrode" terminal 84 of voltage control 66. In the three electrode mode, current does not flow through reference electrode 70. Reference electrode 70 may be used in a three electrode mode of operation to provide a poised, known and stable voltage and is therefore advantageously constructed of silver/silver chloride (Ag/AgCl) or is a saturated calomel electrode (SCE). Voltage control 66 can also be operated in a two electrode mode using only working electrode 56 and electrode 58 as a counter/reference electrode. In this two electrode mode of operation, counter/reference electrode 58 is electrically connected to voltage control terminals 78 and 84 on voltage control 66. In this case, voltage control 66 operates essentially as a battery. Voltage control 66 applies voltage signals to working and counter electrodes 56 and 58 and optionally measures the current flowing through the respective electrodes. Reference electrode 70 may alternatively be a so-called "quasi-reference" electrode constructed of platium, gold, stainless steel or other material, which provides a less stable voltage, but one that is measurable with respect to the solution in contact. In both the two and three electrode modes, the reference electrode 70 or 58 serves the purpose of providing a reference against which the voltage applied to the working electrode(s) is measured. The poised voltage reference is currently considered to be more advantageous. Voltage control 66 in its potentiostat operation controls various electrodes by providing a known voltage at working electrodes 56, 58 with respect to reference electrode 70 while measuring the current flow between working electrodes 56, 58 and counter electrodes 72, 74. Potentiostats for this purpose are well known, and the internal structure of voltage control 66 therefore suitably corresponds to any of the conventional, commercially available potentiostats which produce the above-mentioned functions, and so does not form a part of the present invention per se. Indeed, apparatus 10 can alternatively be constructed without an internal voltage control 66, and can be adapted to be connected to an external potentiostat which is separately controlled for providing required voltage signals to electrodes 56, 58, 72, 74 and 70. These voltage signals, applied in a specific matter as described below, provide repeatable initial conditions for the surfaces of working electrodes 56, 58 and advantageously for the surfaces of cell 12 as a whole, a feature which contributes significantly to improved processing in the measurement of electrochemiluminescence.

Pump 16 is advantageously positioned at outlet 24 to "pull" solution from a sample volume in the direction of arrow A into inlet tube 22. The solution will flow to inlet tube 22, sample-holding volume 30 and outlet tube 24, past reference electrode 70 and out in the direction of arrow B. Alternatively, pump 16 may be positioned at inlet 22 to "push" the solution through apparatus 10. Advantageously, this same flow path through inlet tube 22, sample-holding volume 30 and outlet tube 24 is used for all solutions and fluids which pass through cell 12, whereby each fluid performs a hydrodynamic cleaning action in forcing the pervious fluid out of cell 12. Pump 16 may be controlled to suspend its operation to hold a particular solution in cell 12 for any period of time.

The flow-through construction of apparatus 10 permits working electrodes to be impressed with a variable voltage to be held continuously at a pre-operative potential while being continuously exposed to one or more solutions without exposing working electrodes 56, 58 (or counter and reference electrodes 72, 74, 70) to air. Exposure to air, which opens the circuit to the reference electrode 70, permits unknown, random voltage fluctuation which destroys the reproducibility of surface conditions on working electrodes 56, 58. The flow-through construction permits the rapid alternation between initializing steps, in which electrode system 54 is cleaned and conditioned, and measurement steps, in which one or more measurement waveforms or sweeps trigger electrochemiluminescence.

From the foregoing, it is evident that a composition comprising a metal-containing ECL moiety, an amine or amine moiety, and an electrolyte in accordance with the invention is introduced into cell 12, and exposed to electrochemical energy, advantageously by impressing a suitable voltage on one or more electrodes of the system as described above (or other suitable system as can readily be derived by one of ordinary skill in the art when equipped with the teachings herein) to induce the desired electrochemiluminescence.

The amount of light or other electromagnetic radiation emitted by the reaction system in question is indicative of the presence or absence of an analyte, and, if it is present, in what amount. Thus, qualitative and quantitative analysis of a sample for an analyte of interest is enabled. In this connection, when the electromagnetic radiation emitted is light, that emission can be detected with a photometer which is connected to a computer, e.g., a personal computer. In that computer, the signals received from the photometer are processed and can, for instance, either be displayed on a screen or be outputted via analog conversion onto an appropriate strip-chart or other recorder.

A principal application of the present invention is the detection or quantitation of an analyte of interest in a given sample by ECL assay. As alluded to previously herein, a binding assay involving the ECL reaction of the present invention can be carried out in different formats.

In a first embodiment, a sample which the practitioner desires to investigate for the presence or absence of an analyte of interest is directly evaluated in order to determine whether or not electromagnetic radiation emission is changed (either decreased or increased) with reference to emission obtained from a comparable sample in which none of the ECL moiety present is linked, either directly or through one or more other molecules, to analyte of interest or an analog thereof. In a second embodiment, detection and, if analyte of interest is present, quantitation thereof can be accomplished by taking any steps necessary to formulate an ECL composition in accordance with the present invention from the sample, exposing the composition to electrochemical energy in accordance with the present invention, and then comparing the amount of electromagnetic radiation emitted with the electromagnetic radiation emissions from systems containing various known amounts of the analyte of interest. An appropriate change in emission with the sample being investigated signals the presence and amount of the analyte.

The methods of the invention can be incorporated in a variety of assay formats. Thus the invention may be used in homogeneous or heterogeneous assay formats, and may be used in all assay procedures known in the art, including forward and reverse assays, competition assays, immunometric assays, sandwich assays, and hybridoma screening assays.

As described in commonly assigned U.S. application Ser. No. 266,882, entitled "Electrochemiluminescent Assays", naming Shah, Hall, Powell and Massey as inventors (CMS Docket No. 370068-2390), and filed on even date herewith, it is desirable, in performing assays disclosed herein, to incorporate particles in the assay composition or system. Binding of such a component, which in turn can be linked to an ECL moiety, to the particles greatly modulates the intensity of the ECL signal generated by the ECL moiety, thereby providing a means of monitoring the specific binding reaction of the assay composition or system. Further information on this topic is set forth in the above-mentioned application, the subject matter of which is incorporated herein by reference.

For example, a useful class of homogeneous binding assays provided by the present invention involves exposing a solution of the ECL moiety containing the analyte of interest to an electrode. ECL moiety which cannot gain access to the surface of the electrode will not be detected. This can occur, for example, if the ECL moiety is bound directly or indirectly to the surface of the reaction vessel into which the electrode is placed, or if the ECL moiety is buried deep in the interior of the specific complex, such as within an antigen-antibody complex, or if the electrode itself is coated with a layer through which ECL moiety can pass but ECL moiety linked (directly or indirectly) to the analyte of interest or its analog cannot pass. In addition, it should be possible to coat the surface of an electrode with antibodies, so that only antigen linked directly or through one or more other molecules to the ECL moiety and bound to the immobilized antibodies can obtain access to the electrode and thereby be determined.

Competitive binding methods can be used in accordance with the invention to determine the presence of an analyte of interest. Typically, the analyte and the ECL moiety bind competitively to a chemical material. The material is contacted with the ECL moiety and analyte under suitable conditions so as to form a suitable composition. The ECL moiety is induced to emit electromagnetic radiation by exposing the composition to electrochemical energy. The presence of the analyte of interest is determined by detecting the amount of electromagnetic radiation emitted by the composition.

In competitive binding assays, the analyte of interest or an analog thereof linked directly or through one or more other molecules to an ECL moiety can be any substances capable of participating in formation of a specific complex with a complementary material, such as for example, whole cells, subcellular particles, nucleic acids, polysaccharides, proteins, glycoproteins, lipoproteins, lipopolysaccharides, polypeptides, cellular metabolites, hormones, pharmacological agents, tranquilizers, barbituates, alkaloids, steroids, vitamins, amino acids, sugars and non-biological polymers. Of particular interest are antibody-antigen based methods. These methods are analogous to the well known radioimmunoassay, wherein an analyte of interest is detected when it displaces a radioactive analogue of the analyte from an antibody. The many variations on radioimmunoassay known to the art can, in principle, be used to advantage by employing ECL moieties according to the present invention in place of radioactively labelled compounds.

The invention can also be employed in binding assays used in a competition format, where the ECL moiety is linked directly or through one or more other molecules to added analyte of interest. The binding partner is capable of specifically binding with the analyte of interest or the added analyte of interest which is linked to the ECL moiety. The analyte of interest and the added analyte of interest are suitably an antigen.

Alternatively, the binding partner is a primary binding partner of the analyte of interest. The assay sample contains the ECL moiety linked directly or through one or more other molecules to added analyte of interest. The binding partner is bound to suitable particles in the sample, and the particles are therefore capable of specifically binding with the analyte of interest or the added analyte of interest linked to the ECL moiety. Here also, the analyte of interest and the added analyte of interest are typically an antigen.

The invention can also be used in an immunometric format. The ECL moiety is linked to a binding partner of the analyte of interest. The analyte or an analog thereof is bound to a surface and accordingly the surface is capable of specifically binding with the binding partner. The surface can be the surface of a particle, membrane, strip, tube, etc. The analyte of interest can be an antigen.

Alternatively, the binding partner is a primary binding partner of the analyte of interest. A binding partner of the primary binding partner is a substance linked to the ECL moiety. Analyte or an analog thereof is bound to a surface and accordingly the surface is capable of specifically binding with the primary binding partner. The secondary binding partner linked to the ECL moiety specifically binds the primary binding partner. The analyte of interest is typically an antigen.

The invention can be used, for example, in sandwich assays as well. The analyte of interest can be an antigen. A substance linked to the ECL moiety is a binding partner of the analyte of interest. A binding partner not linked to the ECL moiety is bound to a surface and accordingly the surface is capable of binding to the analyte of interest.

Alternatively, the binding partner may be primary binding partner (BP-1) of the analyte of interest. A secondary binding partner of the primary binding partner is linked to the ECL moiety. The analyte of interest can be an antigen. Another primary binding partner (BP-2) which is not recognized by the secondary binding partner is bound to the surface and accordingly the surface is capable of binding to the analyte of interest. The surface and primary binding partner (BP-1) are capable of specifically binding the antigen and the secondary binding partner linked to the ECL moiety is capable of specifically binding the primary binding partner (BP-1). Also, the binding partner can be a primary binding partner (BP-1) of the analyte of interest. BP-1 is linked to the ECL moiety. Another primary binding partner (BP-1') which is different from BP-1 and binds the analyte of interest is used. A secondary binding partner of the primary binding partner BP-1' is bound to a surface and accordingly the surface is capable of binding the complex of analyte BP-1 and BP-1'.

The methods of the invention are advantageously used in nonseparation binding assays for use in hybridoma screening assay formats. The analyte of interest is a monoclonal antibody directed against a particular antigen. A binding partner of the analyte of interest is linked to the ECL moiety. Antigen is bound to a surface and accordingly the surface is capable of specifically binding with the analyte. The monoclonal antibody specifically binds the surface and the binding partner which is part of the ECL moiety specifically binds the monoclonal antibody.

Advantageously, the binding partner in the ECL moiety capable of specifically binding the monoclonal antibody is a polyclonal antibody, a monoclonal antibody, protein A, or protein G. In addition, that binding partner may be avidin, which can bind to a biotin-modified analyte.

Alternatively, the binding partner is a primary binding partner of the analyte of interest. A binding partner of the primary binding partner is linked to the ECL moiety. The analyte of interest is a monoclonal antibody directed against an antigen. Antigen is bound to a surface and accordingly the surface is capable of specifically binding with the monoclonal antibody. The monoclonal antibody specifically binds the surface, the primary binding partner specifically binds the monoclonal antibody, and the secondary binding partner in the ECL moiety specifically binds the primary binding partner.

The invention is further described and illustrated in the following examples.

EXAMPLES

Electrochemiluminescence measurements were performed with the instrument illustrated in FIG. 1. The equipment utilized in the experiments integrated a photometer, potentiostat, electrochemical cell, and means for fluid control. The cell utilized a conventional three electrode setup and was arranged as a flow-through system. The sequence of operations in the instrument was controlled by an IBM PS/2 Model 25 personnel computer. Data was displayed on the screen or outputted via analog conversion to a X-Y-Y' recorder. The working electrode and counter electrode was a gold disk. The reference electrode, Ag/AgCl, was disposed downstream of the detector apparatus. The photometer employed a red sensitive photomultiplier tube (Hamamatsu, Inc., Middlesex, N.J.). For low light level measurements a photon counting technique was used.

MATERIALS

The following materials were prepared:

A buffer solution, which also contained tripropyl amine, and had the analysis 0.15 molar phoshate, 0.05 molar tripropyl amine ("TPA"), and 0.05% Tween 20, was formulated from 10.21 g of $KH_2PO_4$ (Molecular weight=136.09) and 20.11 g of $Na_2PO_4.7H_2O$ (Molecular weight=268.07) diluted to 990 ml with water with stirring. 9.5 ml of TPA were added with stirring. The pH was adjusted to 7.5 with concentrated $H_3PO_4$. 0.5 ml of Tween 20 were added with stirring.

A stock solution of tris (2,2'-bipyridyl) ruthenium chloride hexahydrate ("Ru(bpy)$_3$ Cl$_2$.6H$_2$O") was prepared by diluting 7.49 mg to 10 ml buffer. The final concentration was 0.001 molar. One-to-ten dilutions of the stock were made with buffer.

Example 1

Cyclic Voltammogram and Simultaneous Emission Profile 1.0 ml of sample ($10^{-9}$M Ru(bpy)$_3$Cl$_2$.6H$_2$O in buffer) was drawn through the instrument and electrochemical cell. The pump was stopped, allowing the solution to come to rest. The potentiostat and cell were turned on. The voltage scan was initiated at 0.0 volts versus a Ag/AgCl reference electrode at a rate of 0.2 V/s. The upper voltage limit was 1.6 volts; the lower voltage limit was −1.0 volts; the final voltage was 0.0 volts. During the scan portion from 0.0 to 1.6 volts, a light emission was detected at about 1.4 volts. The electrochemiluminescense peak intensity from Ru(bpy)$_3$Cl$_2$.6H$_2$O was about 1000 counts. The simultaneous current for the oxidation of TPA was about 0.15 ma. After the scan the electrochemical cell was flushed thoroughly with buffer.

Example 2

Figure 3:
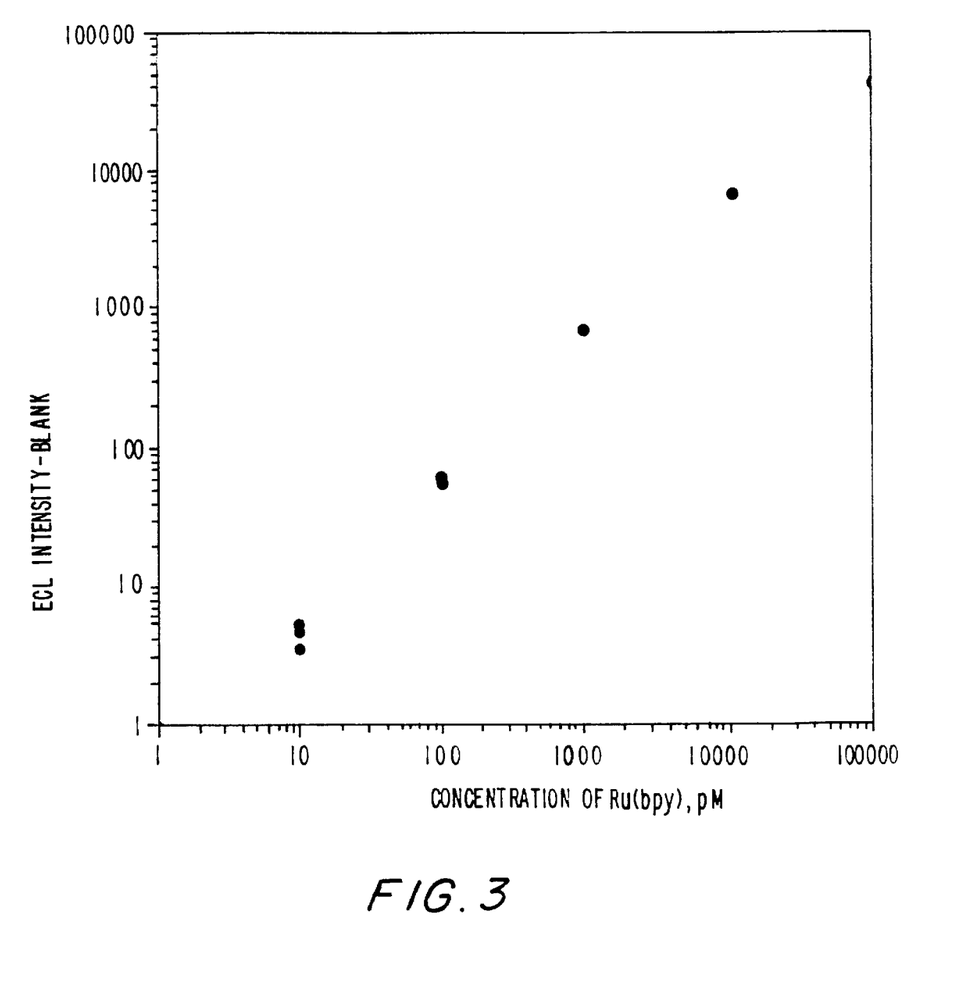
FIGS. 3 and 4 are plots of averaged measurements of ECL intensity obtained at various different concentrations of a ruthenium-containing metal chelate versus the different concentrations.
Figure 4:
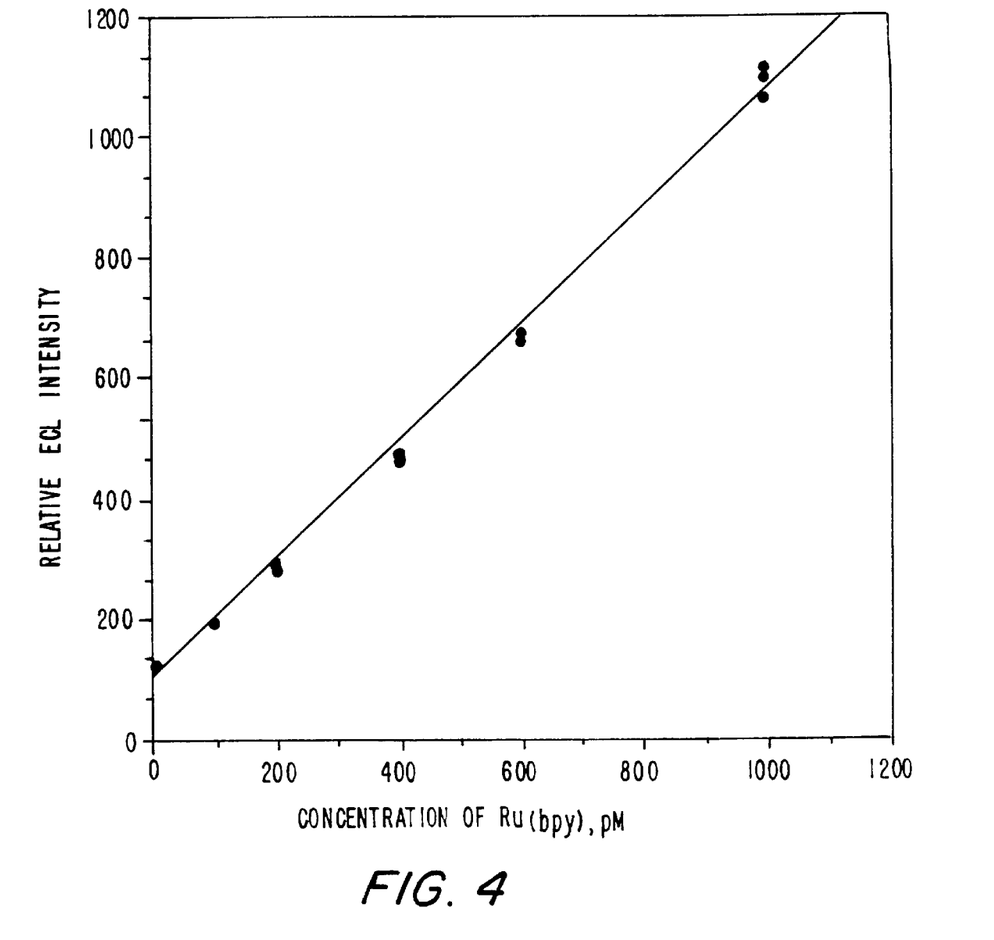

Linear Response of Light Intensity with Ru(bpy)$_3$ Cl$_2$.6H$_2$O Concentrations The buffer solution containing TPA was formulated in the same manner as for Example 1, except that pH was adjusted to 7.0 and 19.0 ml of TPA (0.10M) were used. Varying concentrations of Ru(bpy)$_3$Cl$_2$.6H$_2$O were prepared by simple dilution. Measurements were take on the samples using the same procedure as described in Example 1. Electrochemiluminescence intensity was measured for each concentration of Ru(bpy)$_3$Cl$_2$.6H$_2$O by taking three readings at each such concentration. The average results for each such concentration are presented in FIGS. 3 and 4. FIG. 4 also shows a background intensity observed with a "blank", i.e., a sample without the ruthenium-containing chelate.

Example 3

Effect of TPA Concentrations on Electrochemiluminescence Intensity

Figure 5:
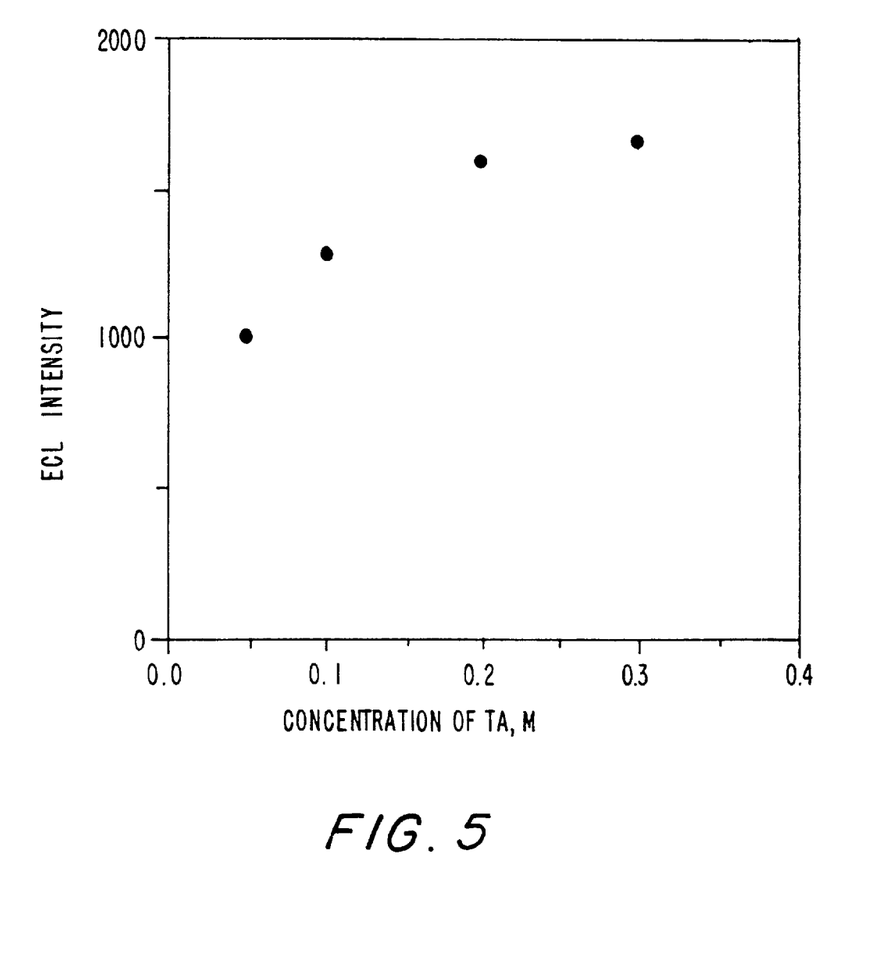
FIG. 5 is a plot of averaged measurements of ECL intensity obtained at different concentrations of tripropyl amine with constant ruthenium-containing chelate concentration.

The buffer solution containing TPA was formulated in the same manner as for Example 1 except that varying amounts of TPA were added and $10^{-9}$M Ru(bpy)$_3$Cl$_2$.6H$_2$O was used. Measurements were taken using the same procedure as described in Example 1. Electrochemiluminescence intensity was measured for each concentration of TPA by taking three readings at each such concentration while holding Ru(bpy)$_3$Cl$_2$.6H$_2$O concentration constant. The averaged results for each such concentration are presented in FIG. 5. Note that readings were normalized to the blank, so as to compensate for background count.

Example 4

Effect of pH on Electrochemiluminescence Intensity

The buffer solution containing TPA was formulated in the same manner as for Example 1, except that the pH was varied, 0.10 molar TPA was used, and $10^{-9}$M Ru(bpy)$_3$Cl$_2$.6H$_2$O was used. Measurements were taken using the same procedure as described in Example 1. Electrochemiluminescence intensity was measured for different pH values at constant Ru(bpy)$_3$Cl$_2$.6H$_2$O concentration by taking three readings at each such pH. The averaged results for each different pH are presented in FIG. 6.

Example 5

The buffer solution containing amine was formulated in the same manner as for Example 1, except that pH was adjusted to 7, the specific amine incorporated was varied in accordance with Table I, and the amine concentration was 100 mM. A solution of Ru(bpy)$_3$Cl$_2$.6H$_2$O of concentration $1\times10^{-8}$M was prepared. Measurements were taken on samples for each different amine in the same manner as described in Example 1. Electrochemiluminescence intensity was measured for each amine by averaging the results of three readings. The data obtained was normalized to a background count obtained with a blank. Table I presents the relative electrochemiluminescence intensities for each amine, the relative intensity amount being the quotient of the intensity measured for the amine divided by the intensity measured for the blank.

TABLE 1

| Amine | Relative Electro-chemiluminescence Intensity |
|---|---|
| tripropyl ammine | 75.1 |
| triethanol amine | 40.0 |
| (1,4-piperazine bis (ethane-sulfonic acid)) | 23.0 |
| 1-piperidine ethanol | 7.0 |
| 1,4 diazabicyclo (2.2.2) octane | 3.4 |
| EDTA | 0.2 |

What is claimed is:

1. A kit for performing an ECL assay wherein electromagnetic radiation emitted by a composition in an excited state is detected, which kit consists essentially of (i) a metal-containing ECL moiety which, when oxidized by exposure to an effective amount of electrochemical energy, is capable of being converted to an excited state from which electromagnetic radiation is emitted upon exposure of the excited ECL moiety to conditions sufficient to induce said emission, (ii) an amine or an amine moiety which, when oxidized by exposure to an effective amount of electrochemical energy, forms a strong reducing agent, and (iii) an electrolyte capable of functioning as a medium in which said ECL moiety and said amine moiety can be oxidized by exposure to electrochemical energy.

2. A kit as defined in claim 1, which comprises a first separate component including any two members of said group and a second separate component including the remaining member of said group and either one of the other members of said group.

3. A kit as defined in claim 1, which comprises three separate components, each of which includes a different one of the three members of said group.

4. A kit as defined in claim 1, which comprises a first separate component including all three members of said group, and a second separate component including any one or two of the members of said group.

5. A kit as defined in claim 1, wherein said second separate component includes one of the three members of said group, and said kit further comprises a third separate component including one or two members of said group.

6. A kit as defined in claim 4, wherein the first separate component includes said ECL moiety (i) and said electrolyte (iii), and said second separate component includes said amine or amine moiety (ii) and said electrolyte (iii).

7. A kit as defined in claim 1, which comprises a first separate component including any two members of said group, and a second separate component including the remaining member of said group.

8. A kit as defined in claim 7, wherein said first separate component includes said ECL moiety (i) and said amine or amine moiety (ii), and said second separate component includes said electrolyte (iii).

9. A kit as defined in claim 7, wherein said first separate component contains said ECL moiety (i) and said electrolyte (iii), and said second separate component contains said amine or amine moiety (ii).

10. A kit as defined in claim 7, wherein said first separate component includes said amine or amine moiety (ii) and said electrolyte (iii), and said second separate component includes said ECL moiety (i).

11. A kit for performing an ECL assay wherein electromagnetic radiation emitted by a composition is detected, which kit consists essentially of (i) a metal chelate which, when oxidized by exposure to an effective amount of electrochemical energy, is capable of being converted to an excited state from which electromagnetic radiation is emitted upon exposure of the excited metal chelate sufficient to induce said emission, (ii) an amine or amine moiety which, when oxidized by exposure to an effective amount of electrochemical energy, forms a strong reducing agent having a redox potential, $E_a$, defined as follows

$$E_a < -hc/\lambda + K + E_m$$

wherein h is Planck's constant, c is the speed of light, $\lambda$ is the wave length characteristic of radiation emitted from the excited state of the metal chelate, K is the product of the absolute temperature in degrees Kelvin and the change in entropy, and $E_m$ is the redox potential of the metal chelate, and (iii) an electrolyte capable of functioning as a medium in which said chelate and said amine or amine moiety can be oxidized by exposure to electrochemical energy.

12. A kit as defined in claim 11, wherein the metal in said metal chelate is a transition metal or a rare earth metal.

13. A kit as defined in claim 11, wherein the metal of the metal chelate is a transition metal.

14. A kit as defined in claim 11, which comprises an amine selected from the group consisting of aliphatic amines, aromatic amines, diamines, polyamines, and such amines substituted by one or more substituents selected from the group consisting of —OH, alkyl, chloro, fluoro, bromo, iodo, —SO$_3$, aryl, —SH, ester groups, ether groups, alkenyl, alkynyl, —N$_2^+$, cyano, epoxide groups and heterocyclic groups, of protonatated salts of the formula R$_3$NH$^+$, wherein R is H or a substituent listed above, and of heterocyclic amines, or comprises an amine moiety derived from one of said substituted or unsubstituted amines.

15. A kit as defined in claim 11, which comprises tripropyl amine or an amine moiety derived therefrom.

16. A kit as defined in claim 11, wherein the electrolyte is aqueous.

17. A kit as defined in claim 11, wherein the electrolyte is non-aqueous.

18. A kit as defined in claim 11, wherein the electrolyte comprises a salt dissolved in water.

19. A kit as defined in claim 11, wherein the electrolyte comprises a phosphate buffer.

20. A kit as defined in claim 11, wherein the electrolyte comprises an organic liquid.

21. A kit as defined in claim 11, wherein the metal chelate is a ruthenium-containing chelate, the amine is tripropyl amine and the electrolyte comprises a phosphate buffer.

22. A kit as defined in claim 11, which is adapted for detection of an analyte selected from the group consisting of whole cell or surface antigen, subcellular particle, virus, prion, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, nonbiological polymer (preferably soluble), synthetic organic molecule, organometallic molecule, tranquilizer, barbituate, alkaloid, steroid, vitamin, amino acid, sugar, lectin, recombinant or derived protein, biotin, avidin, streptavidin, or inorganic molecule present in the sample.

23. A kit as defined in claim 11, which is adapted for detection of an analyte specimen in a concentration of from $10^{-3}$ to $10^{-18}$ molar.

24. A kit as defined in claim 11, wherein the metal of said metal chelate is ruthenium, osmium, rhenium, iridium, rhodium, platinum, indium, palladium, molybedenum, technetium, copper, chromium or tungsten.

25. A kit as defined in claim 24, wherein the metal in said metal chelate is ruthenium or osmium.

26. A kit for detecting or quantitating an analyte of interest by ECL assay wherein electromagnetic radiation emitted by a composition is detected,
  which kit consists essentially of (i) a metal chelate which, when oxidized by exposure to an effective amount of electrochemical energy, is capable of being converted to an excited state from which electrochemical radiation is emitted upon exposure of the excited metal chelate to conditions sufficient to induce said emission, (ii) an amine or an amine moiety which, when oxidized by exposure to an effective amount of electrochemical energy, forms a strong reducing agent, and (iii) an electrolyte capable of functioning as a medium in which said chelate and said amine or amine moiety can be oxidized by exposure to electrochemical energy and (iv) at least one substance selected from the group consisting of (a) additional analyte of interest or an analog of the analyte of interest, (b) a binding partner of the analyte of interest or its said analog, and a reactive component capable of binding with substance (a) or (b).

27. A kit as defined in claim 26, which is adapted for detection of an analyte selected from the group consisting of a whole cell or surface antigen, subcellular particle, virus, prion, viroid, antibody, antigen, hapten, fatty acid, nucleic acid, protein, lipoprotein, polysaccharide, lipopolysaccharide, glycoprotein, peptide, polypeptide, cellular metabolite, hormone, pharmacological agent, nonbiological polymer (preferably soluble), synthetic organic molecule, organometallic molecule, tranquilizer, barbituate, alkaloid, steroid, vitamin, amino acid, sugar, lectin, recombinant or derived protein, biotin, avidin, streptavidin, or inorganic molecule present in the sample.

28. A kit as defined in claim 26, wherein the metal in said metal chelate is ruthenium or osmium.

29. A kit as defined in claim 26, which comprises a first separate component including tripropyl amine and an electrolyte including a phosphate buffer, and a second separate component including a ruthenium-containing chelate.

30. A kit as defined in claim 26, wherein the electrolyte is aqueous.

* * * * *